United States Patent
Kullik

(10) Patent No.: US 6,418,927 B1
(45) Date of Patent: Jul. 16, 2002

(54) ROTARY COMPRESSOR FOR RESPIRATION SYSTEMS

(75) Inventor: Götz Kullik, Lübeck (DE)

(73) Assignee: Dräger Medizintechnik GmbH (DE)

( * ) Notice: Subject to any disclaimer, the term of this patent is extended or adjusted under 35 U.S.C. 154(b) by 0 days.

(21) Appl. No.: 09/354,383

(22) Filed: Jul. 14, 1999

(30) Foreign Application Priority Data

Feb. 3, 1999 (DE) .......................................... 199 04 119

(51) Int. Cl.[7] .............................. A61M 16/00; A62B 7/00
(52) U.S. Cl. .......................... 128/204.18; 128/200.24; 417/423.12; 417/424.2; 415/229; 415/111; 415/112
(58) Field of Search ..................... 128/204.18, 204.22, 128/200.24; 417/423.12, 424.2; 415/229, 111, 112

(56) References Cited

U.S. PATENT DOCUMENTS

| | | | | |
|---|---|---|---|---|
| 3,951,573 A | | 4/1976 | Dunning et al. | |
| 4,460,317 A | * | 7/1984 | Kern et al. | 417/49 |
| 4,764,086 A | * | 8/1988 | Jesinger | 415/112 |
| 5,202,598 A | * | 4/1993 | Katsumata | 310/90 |
| 5,547,350 A | * | 8/1996 | Rawal et al. | 417/354 |
| 5,856,719 A | * | 1/1999 | De Armas | 310/103 |
| 5,868,133 A | * | 2/1999 | De Varies et al. | 128/204.21 |
| 5,875,783 A | | 3/1999 | Kullik | |
| 5,924,847 A | * | 7/1999 | Scaringeet et al. | 417/42 |
| 5,984,627 A | * | 11/1999 | Ramsay | 415/112 |

FOREIGN PATENT DOCUMENTS

JP 10184302 7/1998

* cited by examiner

Primary Examiner—John G. Weiss
Assistant Examiner—Michael Mendoza
(74) Attorney, Agent, or Firm—McGlew and Tuttle, P.C.

(57) ABSTRACT

An improved rotary compressor (1) for respiration systems with breathing gases transported in a closed system. This rotary compressor (1), which can be washed and sterilized, is has an electrically driven compressor wheel (5) mounted by means of an aerodynamic gas slide bearing. The gas slide bearing comprises radially and axially loaded surfaces, wherein either the axially loaded surface (10) of the compressor wheel (5) or the axially loaded, nonmoving housing surface (11) has grooves (22).

21 Claims, 3 Drawing Sheets

ROTARY COMPRESSOR FOR RESPIRATION SYSTEMS

FIELD OF THE INVENTION

The present invention pertains to a rotary compressor for respiration systems. Such respiration systems are used mainly in the area of medicine, where closed respiration systems with rebreathing are used for various reasons.

BACKGROUND OF THE INVENTION

A known field of application in the area of medicine is, in particular, the area of anesthesia, where the circulation of the expired gases and of the newly added gases, e.g., oxygen, is desirable, e.g., in the case of narcotic anesthetics. A rotary compressor for respiration systems, which is particularly suitable because of its properties for rapidly following the spontaneous breathing of the respirated patient, has become known from U.S. Ser. No. 08/965,256. However, such rotary compressors have not yet been able to be sterilized and are therefore unsuitable for use as a gas delivery means in respiration systems with rebreathing in a closed circuit. Furthermore, the separation between the electric components and the breathing gas with increased oxygen concentration is not yet sufficient, so that the oxygen additionally added can be added only in the open respiration system and only behind the rotary compressor and it must therefore be metered dynamically.

SUMMARY AND OBJECTS OF THE INVENTION

The primary object of the present invention is to propose an improved rotary compressor for respiration systems, which can be washed and sterilized, on the one hand, and makes possible a reliable separation of the breathing gas from the electric components, on the other hand.

According to the invention, a rotary compressor for respiration systems is provided with an electrically driven compressor wheel, which is mounted by means of an aerodynamic gas slide bearing.

The gas slide bearing includes axially and radially loaded surfaces. The axially loaded surface of the said compressor wheel may have grooves. The axially loaded, nonmoving housing surface may have grooves. Axial opposite bearing surface of the said compressor wheel may also have grooves. The nonmoving housing surface of the axial thrust bearing may also have grooves. The radially loaded surface of the compressor wheel and/or the radially loaded surface of the thrust bearing of the compressor wheel may have grooves. These grooves may be designed in the form of logarithmic spirals.

The rotation of the compressor wheel may be brought about by the cooperation of a permanent magnet physically connected to the compressor wheel adjacent to the axis of rotation with a magnetic field, which rotates around the axis of rotation and is generated by coils in the radial thrust bearing.

The compressed gas is preferably fed in, in parallel to the said axis of rotation of the said compressor wheel. The compressed gas leaves the compressor wheel at right angles to the axis of rotation.

The compressor may be a radial compressor or side channel compressor.

A method is also provided with a drive for breathing gases transported in closed circuit in a respiration system.

One essential advantage of the present invention arises from the use of the breathing gas itself as a lubricant between the sliding surfaces moving in relation to one another, so that the slide bearing is completely maintenance-free. Due to the design of the aerodynamic gas slide bearing, the rotor and the stator are separated from one another in a completely wear-free manner, and the generation of noise is additionally particularly low compared with prior-art rotary compressors, which is caused by a corresponding stress on the usual rolling bearings because of the relatively high speed of rotation.

In addition, the simple design of the rotary compressor according to the present invention makes it possible to remove, clean, sterilize and reinstall the components through which breathing gases flow during field use, so that use in a respiration system with breathing gases transported in a closed circuit becomes possible in a safe, hygienic and convenient manner.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
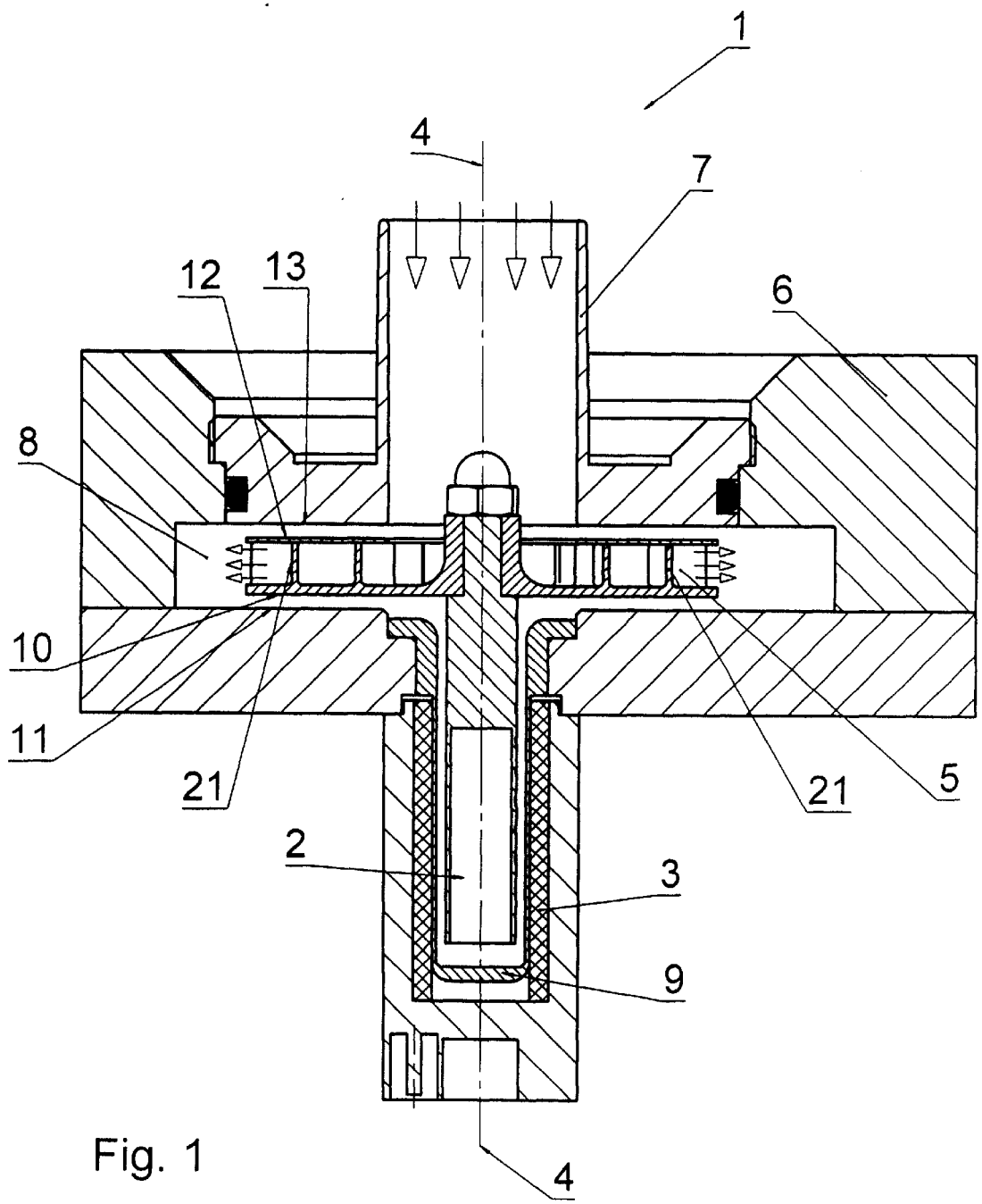
FIG. 1 is a sectional view taken through a rotary compressor according to the present invention, wherein the gaps between parts moving in relation to one another are shown as exaggeratedly wide for illustration.

Referring to the drawings in particular, the rotary compressor 1 according to the present invention, which is shown in a sectional view in FIG. 1 (schematic representation), is driven by means of a brushless, electronically commuted or commutated d.c. motor. The rotor of the d.c. motor is a diametrically magnetized permanent magnet 2, and the stator 3 consists of three coil pairs, one pair of which is shown in a sectional view. The coil pairs are arranged symmetrically to one another at an angle of 120° around the axis of rotation 4, so that the field vector of the coil magnetic field can be rotated around the axis of rotation 4 and thus around the rotor designed as a permanent magnet 2.

The position of the permanent magnet 2 is preferably detected by means of Hall sensors or, during the rotation, by voltages induced in the coils. As a result, the permanent magnet 2, used as the rotor, rotates with the physically connected compressor wheel 5, if current is cyclically applied to the individual coils one after another. The cyclic application of current as a function of the position of the rotor, i.e., the commutation, takes place without wear via semiconductor switching elements, likewise not shown. The rotary compressor 1 is a radial compressor in the exemplary embodiment, but other rotary compressors may also be designed according to the present invention, especially side channel compressors and peripheral compressors.

The compressor wheel 5 connected to the permanent magnet 2 rotates around the axis of rotation 4 by means of the drive explained in the housing 6. The vacuum generated in the intake pipe 7 by the rotation of the compressor wheel 5 causes the transportation of the breathing gas in parallel to the axis of rotation 4 toward the compressor wheel 5, as is indicated by the arrows. The breathing gas is compressed by means of the curved blades 21 shown in FIG. 2, and it finally leaves the compressor wheel 5 at right angles to the axis of rotation 4 via the pressure pipe 8 and flows back into the respiration system 14.

The essence of the present invention is that a completely maintenance-free and practically wear-free mounting of the electrically driven compressor wheel 5 is made available. The breathing self assumes the function of the lubricant for this purpose, i.e., the rotating compressor wheel 5 with the physically connected permanent magnet 2 is mounted by means of an aerodynamic gas slide bearing. Due to the provision of a lubricating wedge in the can 9 arranged in the magnetic gap between the permanent magnet 2 (rotor) and the stator 3, these are separated from one another in a completely wear-free manner, and there is only gas friction between them.

Figure 2A:
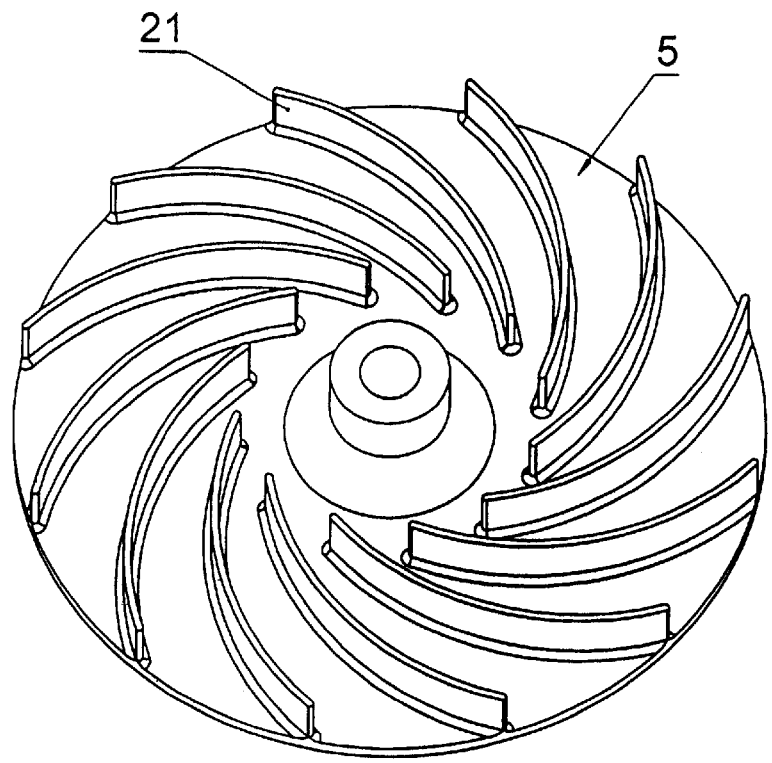
FIG. 2A is a three-dimensional top view of a compressor wheel according to the invention.
Figure 2B:
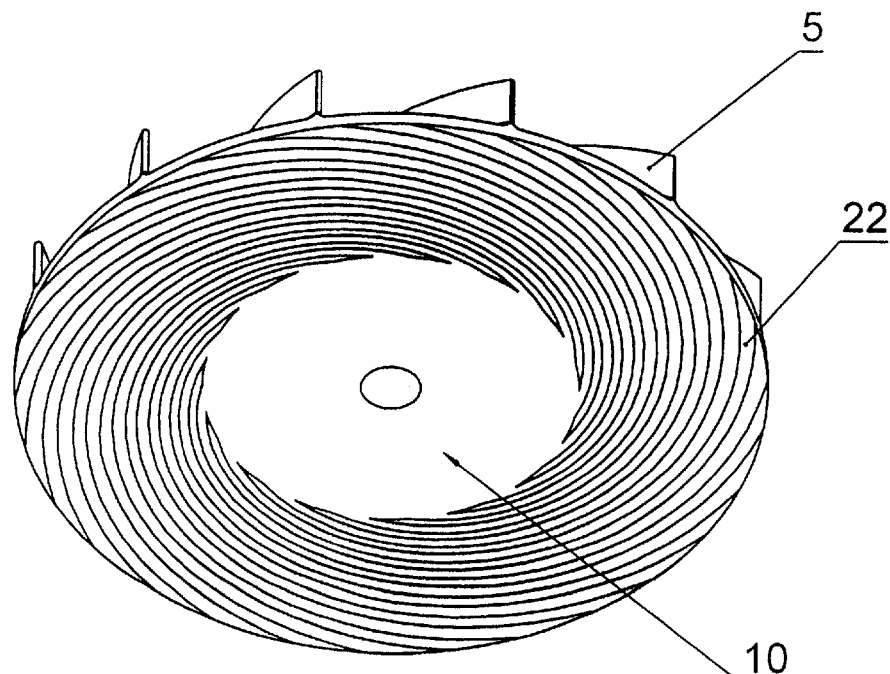
FIG. 2B is a three-dimensional bottom view of the compressor wheel according to the invention.
Figure 2C:
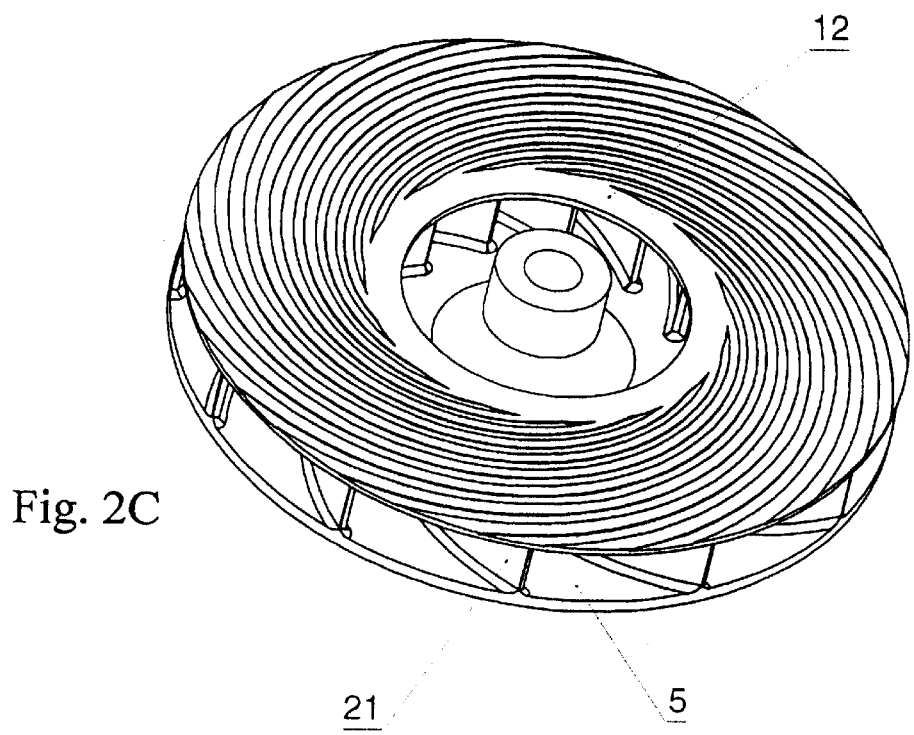
FIG. 2C is a three-dimensional top view of the compressor wheel and the axially opposite bearing surface.
Figure 2D:
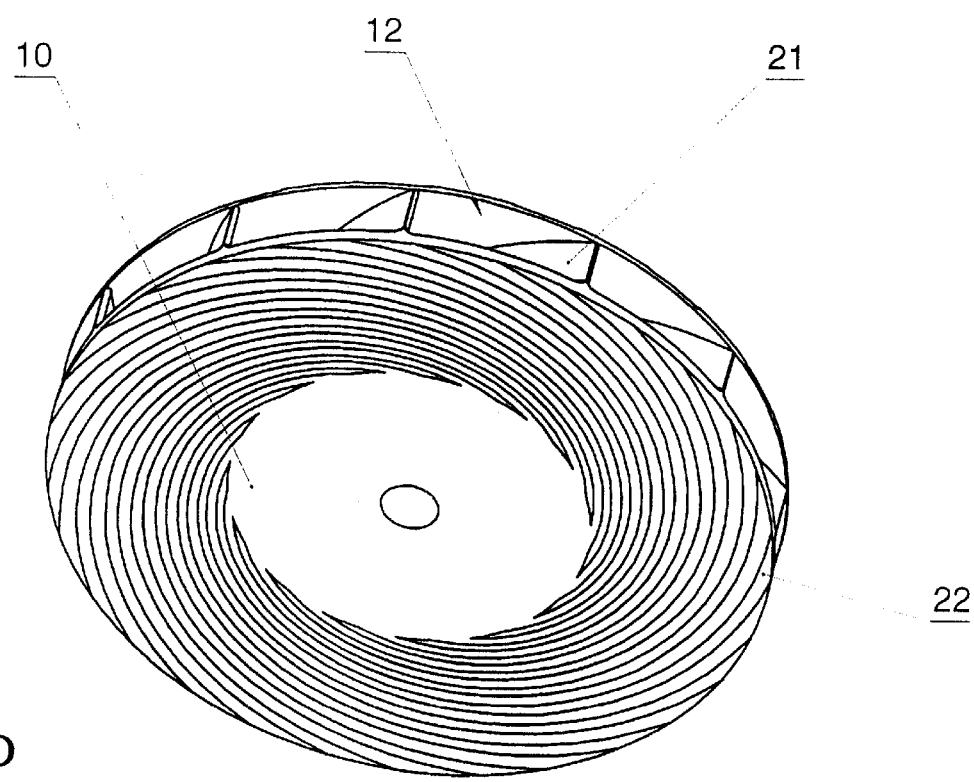
FIG. 2D is a three-dimensional bottom view of the compressor wheel and the axially opposite bearing surface.

The difference in diameter between the stator 3 and the permanent magnet 2 (rotor) is sufficient, in principle, for forming the lubricating wedge for these radially loaded surfaces of the plain bearing designed as a gas slide bearing. However, it has been found that the provision of additional grooves also in the plain bearing increases the load-bearing capacity and the stability. It was surprisingly found in the case of the axially loaded surfaces 10 and 11 (nonmoving housing surface) of the compressor wheel 5 and the opposite wall of the housing 6 that floating with good load-bearing capacity takes place even at a low speed of rotation if the axially loaded surfaces 10 or 11 are designed in the form of grooves 22, as is shown in FIG. 2C for the underside of the compressor wheel (axially loaded surface 10) and FIG. 2D for the axial opposite bearing surface 12 of the compressor wheel 5. For a small radial compressor, the transition between mixed friction and pure gas friction was found at about 190 rpm. The radial compressor was able to be operated without problems above this speed, so that use is practically always possible in the wear-free range of gas friction. In the example shown, the compressor wheel 5 had a diameter of 50 mm and a vertical axis of rotation 4, so that the weight must be supported by a thrust bearing. The axial gas slide bearing is a slide bearing provided with spiral grooves with an external diameter of about 40 mm and an internal diameter of about 20 mm in the example (see FIG. 2), and about 10 to 15 grooves 22 are present, which have a depth of about 25 to 30 $\mu$m and a logarithmic shape, i.e., the grooves 22 form logarithmic spirals with an angle of about 10° to the tangent. The width of the grooves 22 is about 4 to 6 mm.

The axial opposite bearing surface 12 of the compressor wheel 5 preferably also has grooves 22; as an alternative or in addition to this, the nonmoving housing surface 13 of the axial thrust bearing also has grooves 22. As a result, the compressor wheel 5 is prevented from mechanically loading the nonmoving housing surface 13 by friction during the rotation in the case of the vertical axis of rotation 4 shown.

The radial sealing brought about by the can 9 must be able to be magnetically fluxed and must not be electrically conductive, so that no eddy currents are generated. Ceramic and/or plastics are preferred materials. The present invention has led to an electrically driven rotary compressor 1, which is particularly suitable for use in respiration systems with rebreathing and recirculating the breathing gases, because no wearing parts are used, so that the life is practically unlimited. One essential advantage is that the drive element, namely, the compressor wheel 5, can be removed without problems and it can thus be washed and sterilized. In addition, the can 9 between the stator 3 and the rotor (permanent magnet 2) guarantees a hermetic separation between the breathing gas being transported with increased oxygen concentration and the live electric components of the drive, through which current flows.

While a specific embodiment of the invention has been shown and described in detail to illustrate the application of the principles of the invention, it will be understood that the invention may be embodied otherwise without departing from such principles.

What is claimed is:

1. A rotary compressor for respiration systems, the compressor comprising:

a housing;

an electrically driven compressor wheel in said housing;

an aerodynamic gas slide bearing in said housing, said compressor wheel being mounted by said aerodynamic gas slide bearing;

a drive for rotating said compressor wheel to transport breathing gases in the respiration system, said drive including a permanent magnet physically connected to said compressor wheel and forming a rotor of said drive, said compressor wheel and said permanent magnet being removable from said housing for washing and sterilizing of said rotor and said housing.

2. The rotary compressor in accordance with claim 1, wherein said gas slide bearing comprises axially and radially loaded surfaces, and that an axially loaded surface of said compressor wheel has grooves;

said drive includes a stator arranged in said housing, said stator including current and voltage carrying electric components;

a can is arranged between said stator and said rotor to hermetically separate said current and voltage carrying electric components from the breathing gases.

3. The rotary compressor in accordance with claim 2, wherein said gas slide bearing axially loaded surfaces includes one of a nonmoving housing surface having grooves and an axial opposite bearing surface of said compressor wheel having grooves;

said can is electrically nonconductive and can be magnetically fluxed to prevent generation of eddy currents.

4. The rotary compressor in accordance with claim 2, wherein said compressor wheel has a radially loaded surface, one of said compressor wheel radially loaded surface and a radially loaded surface of the bearing has grooves;

said can is formed of ceramic.

5. The rotary compressor in accordance with claim 2, wherein said grooves are designed in the form of logarithmic spirals;

said can is formed of plastic.

6. The rotary compressor in accordance with claim 1, wherein said gas slide bearing comprises axially and radially loaded surfaces including an axially loaded, nonmoving housing surface having grooves.

7. The rotary compressor in accordance with at least one of the claim 1, further comprising an electric drive including a permanent magnet physically connected to said compressor wheel to an axis of rotation, said permanent magnet and coils in the radial thrust bearing generating a magnetic field, which rotates around said axis of rotation.

8. The rotary compressor in accordance with at least one of the claim 1 wherein said gas slide bearing is formed by a housing defining a space for compressed gas to be fed in, in parallel to an axis of rotation of said compressor wheel and for the compressed gas to leaves said compressor wheel at right angles to said axis of rotation.

9. The rotary compressor in accordance with claim 1, wherein the compressor is one of a radial compressor or a side channel compressor.

10. The rotary compressor in accordance with claim 1, wherein:
   said drive includes an electrically commutated d.c. motor, said rotor of said drive being a rotor of said commutated d.c. motor, said d.c. motor including a stator in said housing;
   a can is arranged between said stator and said rotor to hermetically separate said rotor and said stator.

11. A method of recirculating breathing gas to a patient, the method comprising:
   removing breathing gas from the patient;
   feeding the breathing gag from the patient to an intake pipe;
   providing a housing connected to said intake pipe and receiving the breathing gas from the intake pipe;
   providing an rotatable compressor wheel in said housing;
   providing an aerodynamic gas slide bearing between said housing and said compressor wheel to support said compressor wheel aerodynamically when said compressor wheel is rotated;
   providing breathing gases;
   providing a pressure pipe connected to said housing and receiving the breathing gas from said compressor wheel;
   rotating the compressor wheel mounted in the gas slide bearing to transport the breathing from said intake pipe to said pressure pipe gas, said rotating also operating said gas slide bearing to aerodynamically support said compressor wheel in said housing;
   feeding the breathing gas from said pressure pipe to the patient.

12. The method in accordance with claim 11, wherein:
   said rotating of said compressor wheel includes magnetically rotating said compressor wheel without applying electricity to said compressor wheel.

13. A method in accordance with claim 11, further comprising:
   providing a permanent magnet on said compressor wheel;
   providing a plurality of electrical coils in said housing and arranged around said compressor wheel;
   applying current to said plurality of coils in a cyclic application to rotate said compressor wheel in said housing with said housing and said plurality of coils being spaced physically and electrically from said compressor wheel.

14. A closed respiration system for recirculating breathing gas to a patient, the system comprising:
   an intake pipe for receiving the breathing gas from the patient;
   a housing connected to the intake pipe and receiving the breathing gas from the intake pipe;
   a compressor wheel arranged in said housing;
   an aerodynamic gas slide bearing between said compressor wheel and said housing, said gas slide bearing supporting said compressor wheel aerodynamically in said housing when said compressor wheel is rotated in said housing;
   a pressure pipe connected to said housing to receive the breathing gas from from said compressor wheel and feed the breathing gas to the patient.

15. The rotary compressor in accordance with claim 14, wherein:
   said aerodynamic gas slide bearing forms a lubricating wedge between said compressor wheel and said housing, gas between said compressor wheel and said housing forming a lubricant of said lubricating wedge.

16. The rotary compressor in accordance with claim 14, wherein:
   said aerodynamic gas slide bearing forms a gas cushion between said compressor wheel and said housing by rotation of said compressor wheel with respect to said housing, said gas cushion rotatably supporting said compressor aerodynamically in said housing.

17. The rotary compressor in accordance with claim 16, wherein:
   said aerodynamic gas slide bearing includes a plurality of grooves on one of said compressor wheel and said housing for forming said gas cushion through rotation of said compressor wheel.

18. The rotary compressor in accordance with claim 14, further comprising:
   a brushless electronically commutated dc motor connected to said compressor wheel.

19. The rotary compressor in accordance with claim 18, wherein:
   said motor includes a rotor arranged inside said housing and a stator arranged outside said housing, said rotor and said compressor wheel being completely spaced from said housing by a layer of gas formed by said aerodynamic gas slide bearing through rotation of said compressor wheel.

20. The rotary compressor in accordance with claim 19, wherein:
   said motor includes a rotor with a diametrically magnetized permanent magnet, said housing forming a hermetic separation between breathing gas transported by said compressor wheel and electrical components of said motor.

21. The rotary compressor in accordance with claim 20, wherein;
   said aerodynamic gas slide bearing forms an gas cushion between said compressor wheel and said housing by rotation of said compressor wheel with respect to said housing, said gas cushion rotatably supporting said compressor aerodynamically in said housing.

* * * * *